United States Patent
Song et al.

(10) Patent No.: US 10,174,279 B2
(45) Date of Patent: Jan. 8, 2019

(54) APPARATUS AND METHOD FOR EXPANDING SKIN

(71) Applicant: ELECTRONICS AND TELECOMMUNICATIONS RESEARCH INSTITUTE, Daejeon (KR)

(72) Inventors: Yun Jeong Song, Daejeon (KR); Hwi Gang Kim, Daejeon (KR); Jung Wook Suh, Daegu (KR); Eun Chang Choi, Daegu (KR); Chang Hyuk Hong, Daegu (KR); Dae Sik Kim, Daejeon (KR); Hyung Soo Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 43 days.

(21) Appl. No.: 15/215,455

(22) Filed: Jul. 20, 2016

(65) Prior Publication Data
US 2017/0145371 A1 May 25, 2017

(30) Foreign Application Priority Data
Nov. 19, 2015 (KR) ........................ 10-2015-0162247

(51) Int. Cl.
*C12M 1/12* (2006.01)
*C12M 1/34* (2006.01)
*C12M 1/42* (2006.01)

(52) U.S. Cl.
CPC ............ *C12M 35/04* (2013.01); *C12M 25/06* (2013.01); *C12M 41/00* (2013.01)

(58) Field of Classification Search
None
See application file for complete search history.

(56) References Cited

U.S. PATENT DOCUMENTS

| | | | | |
|---|---|---|---|---|
| 5,759,193 | A * | 6/1998 | Burbank | A61B 17/08 606/151 |
| 5,914,264 | A * | 6/1999 | Korman | C12M 21/08 435/283.1 |
| 8,617,181 | B2 | 12/2013 | Sabir et al. | |
| 2012/0028234 | A1 | 2/2012 | Guertin et al. | |

FOREIGN PATENT DOCUMENTS

KR   10-2013-0094314 A    8/2013

* cited by examiner

*Primary Examiner* — Kortney L. Klinkel
*Assistant Examiner* — Stephen M Chong

(57) ABSTRACT

An embodiment of the present invention provides an apparatus and method for expanding skin capable of expanding autologous skin to the maximum extent and performing a tissue culture of skin at the outside of the body. While an apparatus for expanding autologous skin of body's outside in general takes a form of expanding skin by applying a certain amount of constant force for a period of time regardless of the skin properties, the apparatus and method for expanding skin according to the embodiment of the present invention expands the skin to the maximum extent without rupturing the skin based on measurements of elasticity of the skin to find the maximum expanded area reachable just before rupturing of the skin.

5 Claims, 8 Drawing Sheets

APPARATUS AND METHOD FOR EXPANDING SKIN

CROSS-REFERENCE TO RELATED APPLICATION

This application claims priority to and the benefit of Korean Patent Application No. 10-2015-0162247, filed on Nov. 19, 2015, the disclosure of which is incorporated herein by reference in its entirety.

BACKGROUND

1. Field of the Invention

The present invention relates to an apparatus and method for expanding skin, and more particularly, to an apparatus and method for expanding skin which expands autologous skin of the body's outside to the maximum extent to allow culturing of skin tissue.

2. Discussion of Related Art

Generally, skin is one of the organs in a human body and occupies about 16% of the entire body weight. Skin is in direct contact with outside environment and serves a function of protecting a human body from the outside. For example, skin acts as an anatomical barrier against external substances such as pathogens.

In addition, skin provides a semi-permeable barrier that prevents excessive loss of body fluids as well as preventing essential nutrients from being washed away from the body. Other functions of skin may include insulation, regulation of body temperature and sensation.

The skin may be damaged by burns, injuries, disease, depigmentation such as leukoplakia, or the like, and in such cases, the skin damage may be recovered by skin-grafting.

Such a skin-grafting surgery is referring to taking a skin graft from another area, grafting, and suturing at a surgical site with a loss of skin tissue that cannot be closed up by primary suturing and is an essential surgery for cases such as correction of contractures and cicatrices by injuries such as burns, removal of skin tumors and skin ulcers, reconstruction of soft tissue in finger inosculations, etc.

However, in such skin-grafting surgeries, a secondary damage and scar may occur at an area from which the skin is taken, and the surgery may become difficult in cases where the area from which the skin is taken is very small due to prior burns or injuries. Thus, other artificial skin or expanded skin from a small area of skin is used for skin-grafting.

Conventional skin-grafting surgeries may be classified as grafting of artificial skin, grafting using an implantable tissue expander, and a mesh graft, etc. The grafting of artificial skin is a surgery involving grafting an artificially synthesized or cultured skin substitute and needs to be accompanied by grafting of another piece of autologous tissue and limited by short falls in physical properties, expensive cost, a lack of permanency, vulnerability to infections, biological incompatibility, and the like.

Meanwhile, the grafting using an implantable tissue expander is performing surgery after inserting a skin expander in the body to inflate and expand tissues, which is advantageous in terms of using autologous tissues, however requires a lot of time for securing a sufficient quantity of tissues, causes difficulties for daily life, and is not possible to be applied to a body part for which fiberizing of tissue is not suitable.

In addition, the mesh graft surgery is a method of grafting in which a skin graft to be grafted is stretched to a form of mesh using a tool but requires a very long time for recovering the injury, aggravates cicatrices and contractures of the skin, and requires a lot quantity of autologous skin. That is, a skin-grafting surgery capable of minimizing damage and scarring of the donor site, an inadequacy of immunity, and a risk of infection is necessary, and in this connection, an apparatus for expanding skin is necessary which stretches a skin graft of a minimal area collected from a donor site with a certain amount of force at the outside of the body to expand and culture the skin graft to a maximum area possible for the recipient site. A method is necessary for expanding an autologous skin graft to be applied to an affected area of the patient to the maximum extent possible without rupturing the skin by applying an algorithm of expanding skin to the maximum depending on skin conditions of individual patients, skin graft sites to be collected, and expansion environments.

SUMMARY OF THE INVENTION

The present invention is directed to providing an apparatus and method for expanding skin which expands autologous skin to the maximum and performs culturing of the skin tissues at the outside of the body.

Specifically, the present invention is directed to providing an apparatus and method for expanding skin to the maximum extent at which the skin is not ruptured based on checking elasticity of the skin and finding an expandable maximum area of the skin for which the skin is not ruptured from measurements.

According to an aspect of the present invention, there is provided an apparatus for expanding skin which includes a skin graft expansion/culture chamber in which a skin graft is mounted at a plurality of clamps to expand and be cultured, and a driving control unit which drives the clamps of the skin graft expansion/culture chamber to expand the mounted skin graft and controls the driving of the clamps of the skin graft expansion/culture chamber depending on the extent of the expansion of the skin graft.

The plurality of clamps of the skin graft expansion/culture chamber may drive in directions different from each other to expand the skin graft according to the control of the driving control unit.

The plurality of clamps may include an upper plate which comes in contact with an upper surface of the skin graft, a lower plate which comes in contact with a lower surface of the skin graft, and at least one needle which protrudes from at least one of the upper plate and the lower plate and penetrates through the skin graft.

The skin graft expansion/culture chamber may include a clamp module formed to be detachable, and a clamp connection rod connected to the clamp module and each of the clamps and configured to slidingly drive to expand the skin graft mounted at the clamp in directions different from each other.

The driving control unit may modify a position of at least one of the clamp module and the clamp connection rod to control expansion direction and expansion time of the skin graft.

The apparatus for expanding skin may further include a monitoring unit which monitors the extent of the expansion of the skin graft mounted at the clamps of the skin graft expansion/culture chamber.

The driving control unit may include a driving portion which drives the clamp connection rod connected to the clamp module and the clamp to expand the skin graft, a measurement portion which measures the extent of the expansion of the skin graft which expands according to the driving of the driving portion, calculates expanded area of the skin graft according to the extent of the expansion of the skin graft measured, calculates a gradient between a force applied to expand the skin graft and an expanded length of the skin graft, and measures a variation of the gradient, and a control portion which determines whether to control the driving portion according to the result of comparing the variation of the gradient measured and a preset reference range.

The control portion may determine whether the variation of the gradient reaches the point of "0" or "-", control the driving portion to maintain the force level as currently is applied by determining that the skin graft has expanded to the maximum when the variation of the gradient reaches "0" or "-", and control the driving portion to increase the force level depending on the extent to which the skin graft has expanded by determining that the skin graft has not expanded to the maximum when the variation of the gradient has not reached "0" or "-".

According to another aspect of the present invention, there is provided a method for expanding skin which includes mounting a skin graft to a plurality of clamps in a skin graft expansion/culture chamber to expand and culture the skin graft, driving the clamps to expand the mounted skin graft and monitoring the extent of expansion of the skin graft, and controlling the driving of the plurality of clamps in the skin graft expansion/culture chamber according to a result of the monitoring.

The expanding of the skin graft mounted at the clamps of the skin graft expansion/culture chamber may include driving the clamps in different directions from each other according to the driving control to expand the skin graft.

The controlling may include driving the clamps to expand the skin graft mounted by controlling the driving of the clamps, measuring an extent of the expansion of the skin graft which expands according to the driving, calculating an expanded area of the skin graft corresponding to the measured extent of the expansion of the skin graft, calculating a gradient between the force applied to expand the skin graft and the expansion length of the skin graft to measure a variation of the gradient, and comparing the variation of the gradient measured and a preset reference range and determining whether to control the driving of the clamps according to the comparison result.

The determining of whether to control the clamps may include determining whether the variation of the gradient measured has reached "0" or "-", and controlling the driving of the clamps to maintain the force level as is currently applied by determining that the skin graft has expanded to the maximum when the variation of the gradient reaches "0" or "-" as the result of the determination.

The determining of whether to control the clamps may include controlling the driving of the clamps to increase the applied force level depending on the extent to which the skin graft has expanded by determining that the skin graft has not expanded to the maximum when the variation of the gradient is not reached "0" or "-".

BRIEF DESCRIPTION OF THE DRAWINGS

The above and other objects, features and advantages of the present invention will become more apparent to those of ordinary skill in the art by describing in detail embodiments thereof with reference to the accompanying drawings, in which.

DETAILED DESCRIPTION OF EXEMPLARY EMBODIMENTS

Advantages and features of the present invention and methods of accomplishing the same may be understood more readily by reference to the following detailed description of example embodiments and the accompanying drawings. The present disclosure may, however, be embodied in many different forms and should not be construed as being limited to the example embodiments set forth herein. Rather, these example embodiments are provided such that this invention will be thorough and complete and will fully convey the concept of the present invention to those skilled in the art, and the present invention may be defined by the appended claims. Meanwhile, the terminology used herein is for the purpose of describing particular embodiments only and is not intended to limit the present invention. As used herein, the singular forms "a," "an," and "the" are intended to include the plural forms as well, unless the context clearly indicates otherwise. It will be further understood that the terms "comprises," and "comprising" when used herein, specify the presence of stated features, integers, steps, operations, elements, and/or components, but do not preclude the presence or addition of one or more other features, integers, steps, operations, elements, components, and/or groups thereof.

Hereinafter, an apparatus and method for expanding skin according to one embodiment of the present invention will be described in detail with reference to the accompanying drawings.

Figure 1:
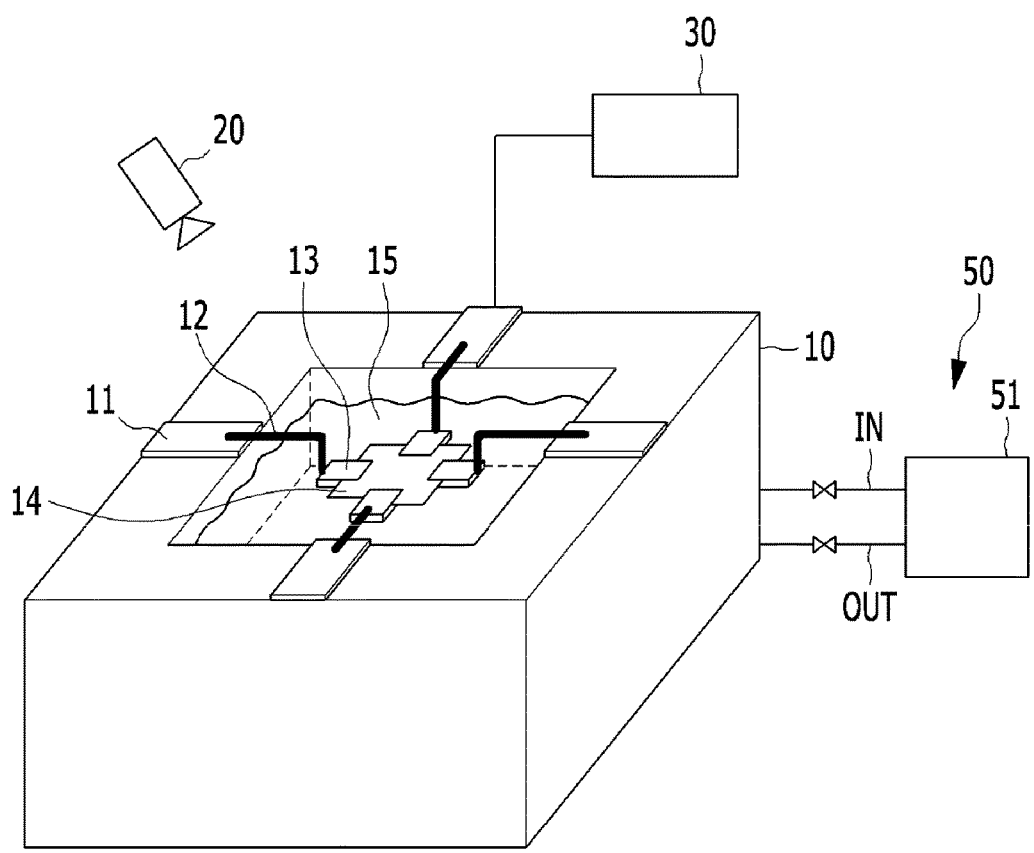
FIG. 1 is a view illustrating a structure and configuration of a driving apparatus for expanding skin according to one embodiment of the present invention.

FIG. 1 is a view illustrating a structure and configuration of a driving apparatus for expanding skin applied to an apparatus for expanding skin according to one embodiment of the present invention.

Referring to FIG. 1, the apparatus for expanding skin according to one embodiment of the present invention may include a skin graft expansion/culture chamber 10 containing a culture medium 15 in which a skin graft 14 is soaked, an environment control unit 50 connected to the skin graft expansion/culture chamber 10 and configured to control the environment in the skin graft expansion/culture chamber 10, a clamp unit having a plurality of clamps 13 for clamping the skin graft 14 soaked in the culture medium 15, and a driving control unit 30 that drives the clamp unit.

The skin graft 14 is used for restoring skin damage and refers to one removed from human skin. The skin graft may be obtained from surgically removing a part of his/her own skin or from surgically removing a part of skin of another person, and the skin graft 14 obtained as described above may be used for grafting onto damaged skin of a patient.

The skin graft 14 may be obtained by various known methods and, for example, may be obtained by marking an extent of an area at a donor site and cutting the skin of the marked area. For various other methods of the known skills, detailed descriptions thereof will be omitted.

The skin graft expansion/culture chamber 10 provides a space in which an expansion of the skin graft is performed and may provide a space with an upwardly open shape. In this case, the skin graft expansion/culture chamber 10 may include a bottom surface and side wall portions which upwardly extend from the bottom surface.

The skin graft 14 is soaked in the culture medium 15, and culturing is concurrently performed with the expansion. The culture medium 15 may be further added or replaced with a new culture medium as needed while the expansion of the skin graft 14 is performed or after performing the expansion.

The culture medium 15 is for culturing the skin graft 14 and may include macroelements and trace elements required for the cell growth of the skin graft 14. A known composition of the culture medium 15 may be used, and there is no particular limit.

The environment control unit 50 controls an environment inside of the skin graft expansion/culture chamber 10, especially the environment related to temperature.

It is preferable that the culture medium 15 in the skin graft expansion/culture chamber 10 be maintained at a temperature at which the skin graft 14 is easily cultured. The environment control unit 50 may include a heater (not shown) which transfers heat to the skin graft expansion/culture chamber 10 and transfers heat to the culture medium 15 so that the culture medium 15 maintains a predetermined temperature, for example, substantially the same temperature as a body temperature.

According to one embodiment of the present invention, the environment control unit 50 may be installed inside the side wall portion of the skin graft expansion/culture chamber 10 and include a water channel (not shown) through which warm water flows, a water inlet IN for supplying warm water to the water channel, and a water outlet OUT which drains warm water from the water channel. The side wall portion may have a double wall structure having an inner wall and an outer wall.

However, the shape of the water channel in the side wall portion may be other diverse shapes. For example, the water channel may be provided in a tube shape and may be bent several times.

The water inlet IN is connected to one side of the water channel and provides warm water from the outside to the water channel. A feed valve may be installed at the water inlet IN through which a quantity and speed of the warm water supplied via the water inlet IN may be regulated.

The water outlet OUT is connected to the other side of the water channel and drains warm water from the water channel to the outside. A drain valve may be installed at the water outlet OUT through which a quantity and speed of the warm water drained via the water outlet OUT may be regulated.

According to one embodiment of the present invention, a circulation pump 51 may be connected to one side of the water inlet IN. The circulation pump 51 may pump the warm water in a direction of the water inlet IN. According to one embodiment of the present invention, the circulation pump 51 may also be connected to the water outlet OUT, and in this case, the circulation pump 51 reheats the drained water from the water outlet OUT and supplies the heated water back in the direction of the water inlet IN.

The environment control unit 50 supplies the warm water to the water inlet IN by the circulation pump 51, and the warm water supplied via the water inlet IN moves in the water channel in the side wall of the skin graft expansion/culture chamber 10 and then drains through the water outlet OUT. The warm water transfers heat to the culture medium 15 of the skin graft expansion/culture chamber 10 while moving in the water channel. The warm water drained from the water outlet OUT may be supplied back to the water inlet IN by the circulation pump 51.

Although not illustrated in the drawings, a heating member for heating the warm water may be provided at the side of the circulation pump 51.

According to the embodiment of the present invention, the configuration of the environment control unit 50 is not limited thereto and may be provided with other configurations as long as it controls a temperature environment of the skin graft expansion/culture chamber 10. For example, the environment control unit 50 may be provided with a form of heating coil provided in the side wall portion of the skin graft expansion/culture chamber 10.

The clamp portion is for expanding the skin graft 14 while soaked in the culture medium 15 and stretches the skin graft 14 in outward directions to apply a tensile force to the skin graft 14.

The clamp portion may include a clamp 13 for clamping the skin graft 14, a clamp connection rod 12 connected to the clamp 13, and a clamp module 11 for connecting the clamp connection rod 12 and the skin graft expansion/culture chamber 10.

The clamp 13 is provided with multiple clamps and directly grabs the skin graft 14. For example, the clamp 13 is provided with at least two clamps to grab opposite ends of the skin graft 14 facing each other. The clamps 13 grab opposite ends of the skin graft 14 facing each other and simultaneously draw the skin graft 14 in outward directions to apply a tensile force to the skin graft 14.

Figure 2A:
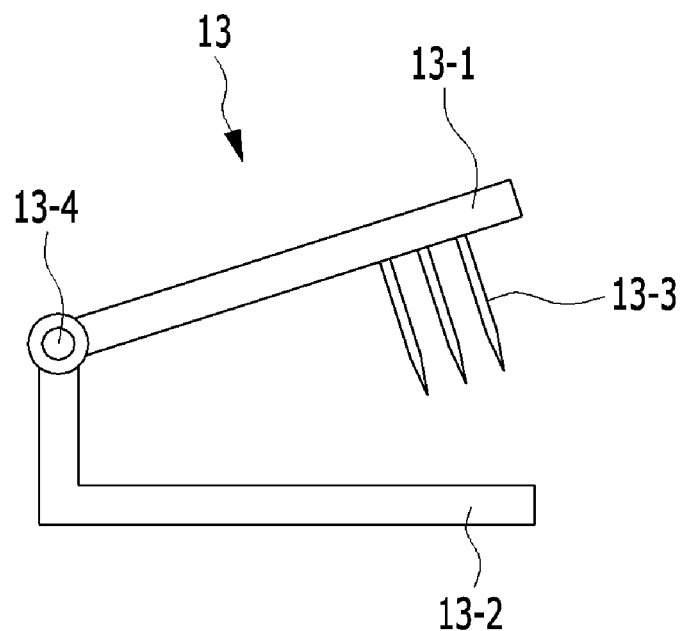
FIG. 2A is a cross-sectional view illustrating a clamp according to one embodiment of the present invention.
Figure 2B:
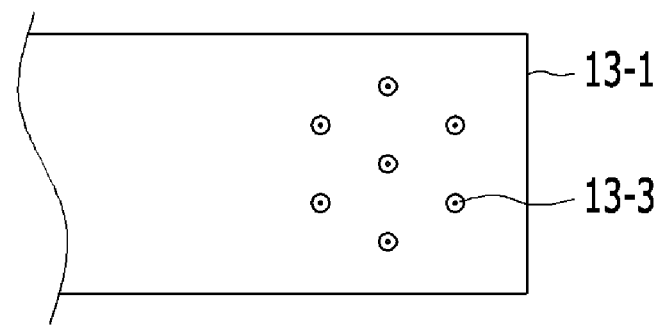
FIG. 2B is a plan view of an upper plate of FIG. 2A.
Figure 2C:
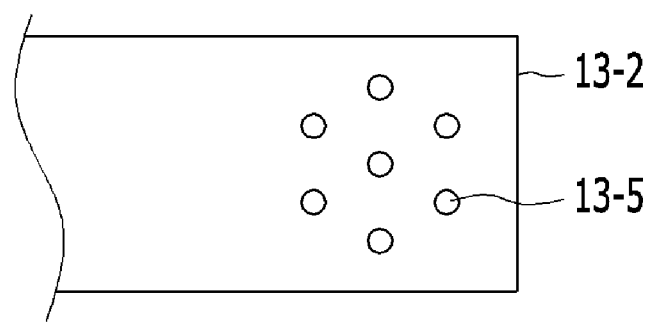
FIG. 2C is a plan view of a lower plate of FIG. 2A.

FIG. 2A is a cross-sectional view illustrating a clamp according to one embodiment of the present invention, FIG. 2B is a plan view of an upper plate of FIG. 2A viewed from the bottom, and FIG. 2C is a plan view of a lower plate of FIG. 2A viewed from the top.

Referring to FIG. 1 and FIGS. 2A to 2C, each of the clamps 13 may include an upper plate 13-1 in contact with a top surface of the skin graft 14, a lower plate 13-2 in contact with a bottom surface of the skin graft 14, and needles 13-3 which protrude from at least one of the upper plate 13-1 and the lower plate 13-2 and penetrate through the skin graft 14.

The upper plate 13-1 and the lower plate 13-2 are connected through a pivot 13-4, and at least one of the upper plate 13-1 and the lower plate 13-2 may rotationally move about the pivot 13-4 to some degree.

For the clamps 13 of the embodiment of the present invention, the upper plate 13-1 and the lower plate 13-2 open up for the skin graft 14 to enter and may be sufficiently pressed against each other after the skin graft 14 is entered so that the needle 13-3 sufficiently enters into the skin. That is, the upper plate 13-1 and the lower plate 13-2 are disposed with the skin graft 14 interposed therebetween, and are fixed by the needles 13-3. When the skin graft 14 is grabbed by the clamps 13, a lower surface of the upper plate 13-1 may come in direct contact with the upper surface of the skin graft 14, and an upper surface of the lower plate 13-2 may come in direct contact with the lower surface of the skin graft 14.

The needles 13-3 fix the skin graft 14 between the upper plate 13-1 and the lower plate 13-2 by penetrating through the skin graft 14. One embodiment of the present invention illustrates that the needles 13-3 protrude in a direction from the upper plate 13-1 to the lower plate 13-2, but the direction is not limited thereto, and the needles 13-3 may protrude in a direction from the lower plate 13-2 to the upper plate 13-1.

In one embodiment of the present invention, damage of the grabbed skin graft 14 may be minimized by using the needles 13-3. The needles 13-3 are applied to a tiny area in the area of the skin graft 14 and are stuck to the skin graft 14 in a direction perpendicular to the direction in which the tensile force is applied to the skin graft 14, and thereby damage to the skin is minimized in the stage of expanding the skin graft 14.

In addition, the skin graft 14 is not easily separated from the clamp 13 owing to the needles 13-3.

One or the plurality of needles 13-3 may be provided in one embodiment of the present invention.

When the plurality of needles 13-3 are provided, the needles 13-3 may be arranged in various forms to efficiently grab the skin graft 14 as well as minimize damage of the skin graft 14. For example, the needles 13-3 may be arranged in a staggered array in a zigzag form with respect to a direction in which the skin graft is stretched. This is for preventing damage that may occur when the tensile force applied to the skin graft is concentrated on a particular part.

Guide holes 13-5 which respectively correspond to positions at which the needles 13-3 are provided may be provided at the lower plate 13-2. The needles 13-3 enter into the guide holes 13-5 when the clamp is closed.

The guide hole 13-5 guides a moving path of the needle 13-3 and simultaneously prevents wear of a needle point during closing of the clamp.

Shapes of the upper plate 13-1, the lower plate 13-2, the needle 13-3, and the pivot 13-4 of the clamp 13 in one embodiment of the present invention may be diversely modified within the scope of the principle of fixing the skin graft 14.

The clamp connection rod 12 is provided in a rod form with one end connected to the clamp 13 and the other end connected to the clamp module 11. The clamp connection rod 12 may be bent several times as needed. The clamp connection rod 12 may have a plurality of columns connected to each other at a bent portion, and in this case, the clamp connection rods 12 may be engaged to each other at the bent portion. Accordingly, each bent and separated portion of the clamp connection rods 12 may be adjusted in length or position and may be engaged with adjacent portions separated from each other. For example, the pivot 13-4 may be provided to the clamp connection rods 12 at the bent position.

The clamp connection rod 12 driven by the driving control unit 30 may position the skin graft 14 as closely as possible to a bottom of the skin graft expansion/culture chamber 10. In this case, a large quantity of the culture medium 15 is unnecessary, and thereby the quantity of the culture medium 15 used may be minimized.

The clamp module 11 is connected to the clamp connection rod 12 and may be provided at an upper portion of the skin graft expansion/culture chamber 10. Specifically, the clamp module 11 may be provided at an upper portion of the side wall of the skin graft expansion/culture chamber 10. The clamp module 11 may include a magnet (not shown) and may be attached to and detached from the skin graft expansion/culture chamber 10 using magnetic force.

The driving control unit 30 which controls the driving of the clamp unit controls expansion direction and expansion time of the skin graft 14 by modifying at least one of the clamp module 11 and the clamp connection rod 12.

For example, the driving control unit 30 may move the clamp modules 11 toward at least one of the directions perpendicular to gravity, i.e., horizontal directions, or move the clamp connection rod 12 toward a direction parallel to the gravity.

In addition, the driving control unit 30 may control the clamp modules 11 to move forward or backward in one direction. The driving control unit 30 may have a sliding structure of a cylinder type to modify positions of the clamp modules 11 and the clamp connection rod 12.

In consideration of the expansion direction of the skin graft 14, the clamp module 11 may move on the side wall of the skin graft expansion/culture chamber 10 in a predetermined direction, for example in a horizontal direction. Also, in consideration of the expansion direction of the skin graft 14, the clamp connection rod 12 at the portion at which the clamp module 11 is connected with the clamp 13 may move in a predetermined direction, for example in a horizontal direction or vertical direction.

According to one embodiment of the present invention, the apparatus for expanding skin may further include a camera 20. The camera 20 may remotely observe, record, or capture images of the extent to which the skin graft 14 expands and is cultured. In one embodiment of the present invention, a state of the skin graft 14 may be monitored via the camera 20, and whether a further expansion or culturing for the skin graft is needed may be determined.

The apparatus for expanding skin having the above-described configuration expands the skin graft 14 using the clamp unit and simultaneously performs culturing of the skin graft 14, and thereby a skin graft 14 having a larger area than the initially collected skin graft 14 may be obtained.

Figure 3:
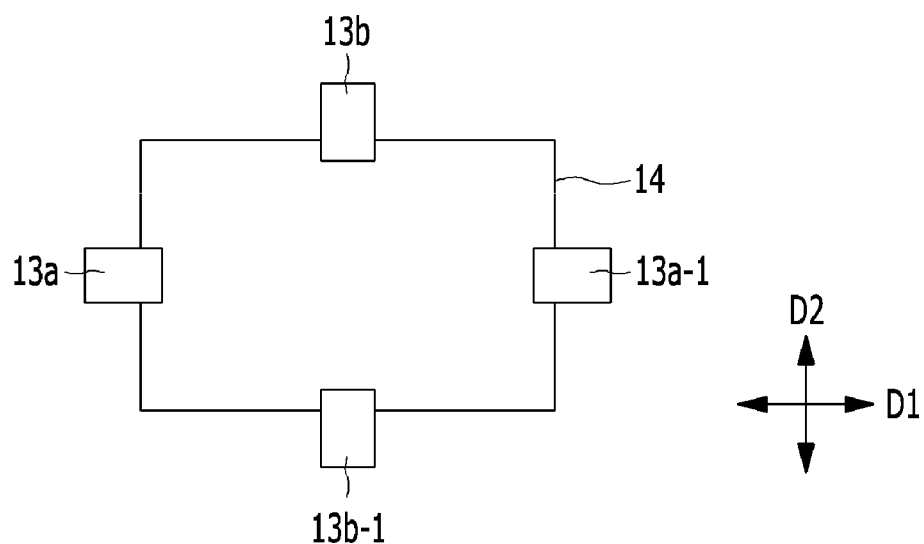
FIGS. 3 to 6 illustrate various types of different embodiments of connection structures between a skin graft and clamps of the embodiment of the present invention shown in FIG. 1.

FIG. 3 is a plan view illustrating a portion of the apparatus for expanding skin shown in FIG. 1, and only the clamps and the skin graft which is the object of the expansion in the apparatus for expanding skin of the present invention are illustrated.

Referring to FIG. 3, the skin graft 14 for expanding is fixed by the clamps 13a, 13b, 13a-1, and 13b-1. Here, the skin graft 14 is provided in a rectangular form but is not limited thereto and may have diverse forms such as a circle, an oval, a semicircle, and a polygon including a triangle.

The clamps 13a, 13b, 13a-1, and 13b-1 may include a first clamps 13a and 13a-1 disposed at opposite ends of the skin graft 14 in a first direction D1 and a second clamps 13b and 13b-1 disposed at opposite ends of the skin graft 14 in a second direction D2. The second direction D2 and the first direction D1 are directions different from each other and may intersect perpendicular to each other.

The first clamps 13a and 13a-1 facing each other stretch the skin graft 14 to the outside in the first direction D1 to apply a tensile force to the skin graft 14 in the first direction of D1. Here, the shapes of the first clamps 13a and 13a-1 which face each other may be identical. As the skin graft 14 is soaked in the culture medium, culturing the skin graft 14 is simultaneously progressed while expanding the skin graft 14 toward opposite ends of the first direction D1.

The second clamps 13b and 13b-1 facing each other stretch the skin graft 14 toward the outside in the second direction D2 to apply a tensile force to the skin graft 14 in the second direction of D2. Here, the shapes of the second clamps 13b and 13b-1 which face each other may be identical. As the skin graft 14 is soaked in the culture medium, culturing the skin graft 14 is simultaneously progressed while expanding the skin graft 14 toward opposite ends of the second direction D2.

As described above, a skin graft 14 having a larger area than the initially collected skin graft 14 may be obtained by expanding the skin graft 14 in the first direction D1 and the second direction D2 using the first clamps 13a and 13a-1 and the second clamps 13b and 13b-1.

As the number and positions of the first clamps 13a and 13a-1 and the second clamps 13b and 13b-1 may be differently set according to the shape of the skin graft 14 or expanding directions, descriptions thereof will be described with reference to FIGS. 4 and 5.

Figure 4:
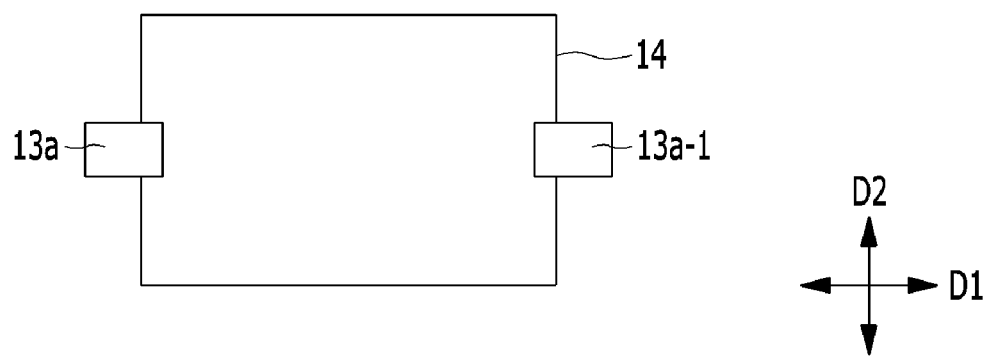
Figure 5:
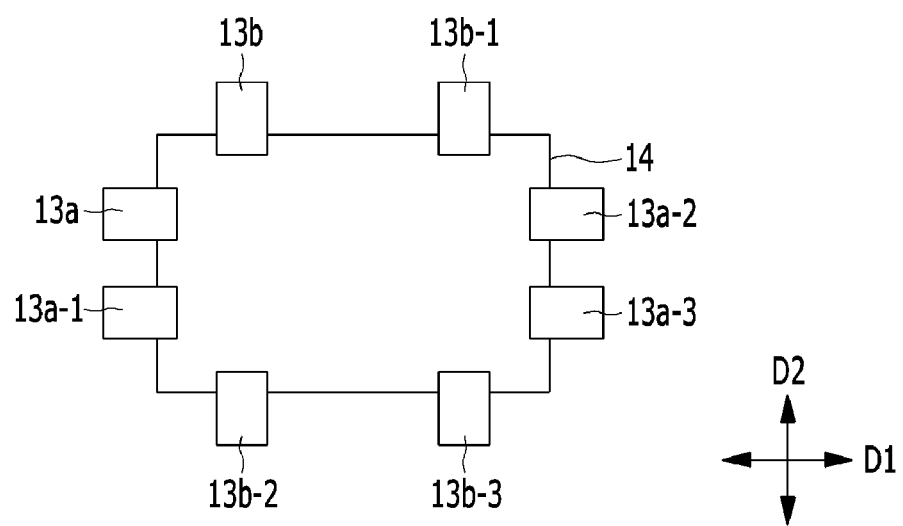
Figure 6:
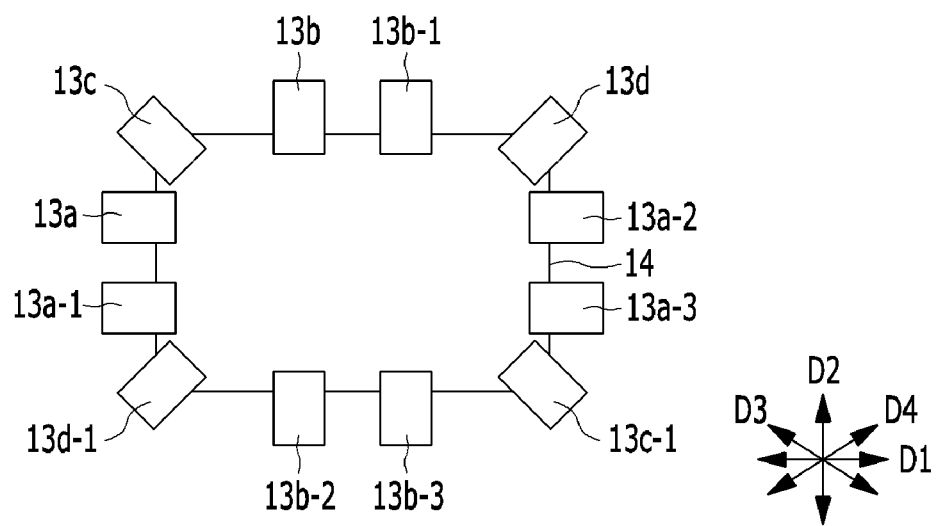

FIGS. 4 to 6 are plan views each illustrating apparatus for expanding skin according to other embodiments of the present invention, and only the clamps and the skin graft which is the object of the expansion in the apparatus for expanding skin of one embodiment of the present invention are illustrated.

Referring to FIG. 4, the skin graft 14 in the apparatus for expanding skin according to one embodiment of the present invention is only fixed by the first clamps 13a and 13a-1 positioned at opposite ends of the first direction D1.

In the embodiment, the skin graft 14 only expands toward the outside of the opposite ends thereof in the first direction D1 and does not expand toward any other direction besides the first direction D1.

Referring to FIG. 5, the skin graft 14 in the apparatus for expanding skin according to one embodiment of the present invention may be fixed by the clamps which include a first clamps 13a, 13a-1, 13a-2, and 13a-3 disposed as pairs at one end and the other end of the skin graft 14 in the first direction D1, and a second clamps 13b, 13b-1, 13b-2, and 13b-3 disposed as pairs at one end and the other end of the skin graft 14 in the second direction D2. Here, each pair of the clamps facing each other with the skin graft 14 interposed therebetween, that is, 13a and 13a-2, 13a-1 and 13a-3, 13b and 13b-2, and 13b-1 and 13b-3, stretch the skin graft 14 toward the outside direction of the skin graft 14 at positions different from each other, and thereby the skin graft 14 may efficiently expand in the directions D1 and D2.

Referring to FIG. 6, the skin graft 14 in the apparatus for expanding skin according to one embodiment of the present invention may be fixed by the clamps which include a third clamps 13c and 13c-1 at opposite ends of the skin graft 14 in a third direction D3 which crosses the first direction D1 and the second direction D2 and a fourth clamps 13d and 13d-1 at opposite ends of the skin graft 14 in a fourth direction D4 which crosses the first direction D1 and the second direction D2 and simultaneously crosses the third direction D3 in addition to the first clamps 13a, 13a-1, 13a-2, and 13a-3 disposed as pairs at one end and the other end of the skin graft 14 in the first direction D1 and the second clamps 13b, 13b-1, 13b-2, and 13b-3 disposed as pairs at one end and the other end of the skin graft 14 in the second direction D2. In this case, the skin graft may more easily expand by the first to the fourth clamps which apply a tensile force in directions different from each other.

Referring to FIGS. 3 to 6, the clamps may be provided in various directions and numbers depending on directions to which the skin graft expands. In other words, the tensile force may be applied to the skin graft in one direction along a single axis as illustrated in FIG. 4 and may be applied in multiple directions along multiple axes as illustrated in FIGS. 3, 5 and 6.

The configuration and detailed operation of the apparatus for expanding skin according to the embodiments of the present invention as described above will be described below with reference to FIG. 7.

Figure 7:
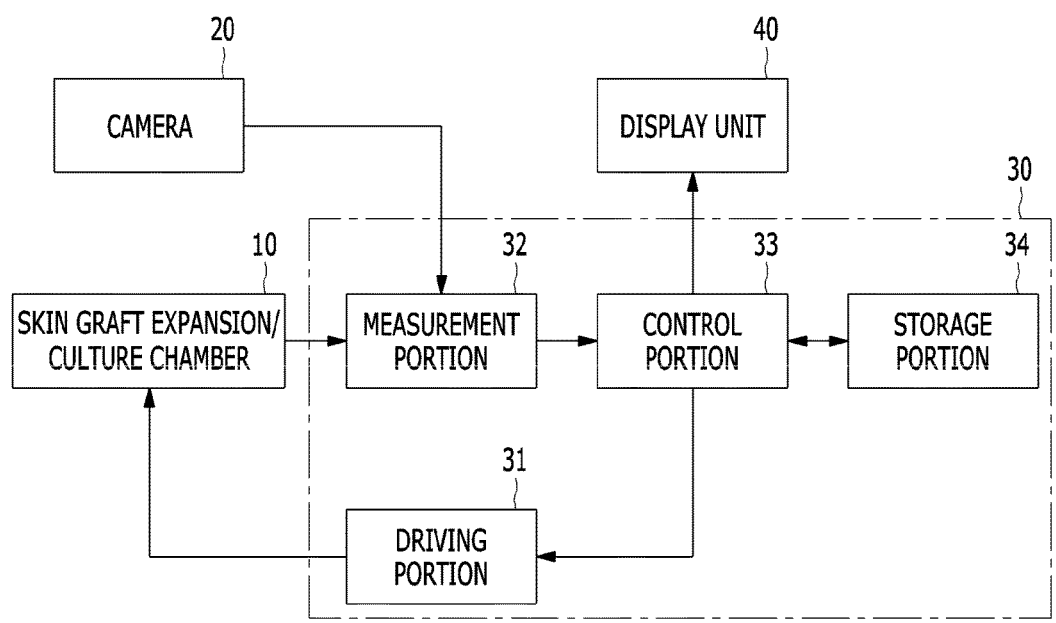
FIG. 7 is a block diagram illustrating the apparatus for expanding skin according to the embodiment of the present invention.

FIG. 7 is a block diagram of the apparatus for expanding skin according to the embodiment of the present invention.

As illustrated in FIG. 7, the apparatus for expanding skin according to the embodiments of the present invention may include the skin graft expansion/culture chamber 10, the camera 20, and the driving control unit 30 shown in FIG. 1, and a display unit 40. Here, as the skin graft expansion/culture chamber 10 has been described with reference to FIG. 1, the configuration and connection structure thereof will be omitted.

The driving control unit 30 includes a driving portion 31, a measurement portion 32, a control portion 33, and a storage portion 34.

When the skin graft 14 is mounted at each of the clamps 13 of the skin graft expansion/culture chamber 10, the driving portion 31 drives the clamp connection rod 12 connected to the clamp module 11 and the clamp 13 by the control of the control portion 33. Here, at an initial time of the driving, the driving portion 31 is controlled so that a predetermined driving force is applied to the clamp connection rod 12.

Then, the driving portion 31, by the control of the control portion 33, increases the force applied to the clamp connection rod 12 so that the mounted skin graft 14 is tightened.

The process in which the skin graft expands as described above is imaged by the camera 20 and the image is provided to the measurement portion 32.

The measurement portion 32 measures the extent to which the skin graft 14 has expanded through the expansion images of the skin graft 14 input from the camera 20 or measures the extent to which the skin graft 14 according to the amount of movement of the clamp connection rod 12 and then provides the control portion 33 with the information of the extent to which the skin graft 14 has expanded as measured or observed as above.

The control portion 33 calculates a gradient between the expansion length provided from the measurement portion 32 according to the extent to which the skin graft 14 has expanded and the force applied to the clamp connection rod 12 of the skin graft expansion/culture chamber 10 provided through the driving portion 31 and checks the amount of variation for the calculated gradient.

In addition, the control portion 33 may store in the storage portion 34 information on the force of the driving portion 31 applied to the clamp connection rod 12, or store in the storage portion 34 the image information of the extent to which the skin graft 14 expands imaged by the camera 20 and/or display through the display unit 40.

Meanwhile, the control portion 33 determines whether the gradient variation of the force versus expansion length of the skin graft 14 checked as above falls within the predetermined range. That is, through the variation of the gradient, the control portion 33 determines whether the saturation point of the tensile force on the skin graft 14, for example, the point at which the gradient becomes "0" or "-" is reached.

As the result of determination, when the variation of the gradient reaches "0" or "-", the control portion 33 determines that the skin graft 14 has expanded to the maximum extent and controls the driving portion 31 to maintain the force level as is currently applied.

However, when the variation of the gradient has not reached "0" or "-", the control portion 33 determines that the skin graft has not expanded to the maximum extent and then controls the driving portion 31 to increase the force being applied to the clamp connection rod 12 depending on the extent to which the skin graft 14 has expanded.

As described above, when the variation of the gradient reaches "0" or "-" and hence the skin graft 14 is determined to have expanded to the maximum extent, the culturing process of the expanded skin graft 14 starts at the point. Here, the culturing process of the skin graft 14 has been described in detail in the descriptions of FIG. 1 and will be omitted.

Detailed operation of the above-described apparatus for expanding skin according to the embodiment of the present invention will be described below.

First, the skin graft 14 is mounted or fixed to the clamp 13, and the driving portion 31 applies a predetermined level of force, i.e., a low level, according to the control of the control portion 33.

Next, the measurement portion 32 measures the extent to which the skin graft 14 has expanded through a camera 20 or by measuring an amount of movement of the clamp connection rod 12 attached to the clamp module which fixes and stretches the skin graft 14 while the driving portion 31 gradually increases the force according to the control of the control portion 33.

Next, the control portion 33 calculates a correlation between the extent to which the skin graft 14 expands measured by the measurement portion 32 and pressure, that is, calculates the gradient, checks whether the calculated gradient is "+", and continues to increase the force to expand the skin graft 14 when the gradient is "+".

After repeating the above-described process, when the gradient is "0" or less, the driving control unit 30 determines that the expansion of the skin graft 14 has reached the saturation state, ceases the expansion, and fixes the pressure. Through this process, the skin graft may continuously expand to a maximum extent just before the skin graft is ruptured.

Then, the pressure is fixed to be constant for a certain amount of time and culturing of the skin graft 14 progresses. After this, the skin graft expands and is cultured starting from the base pressure and repeating the above-described procedures.

The measurement portion 32 receives information on the extent to which the skin graft 14 expands from an amount of variation of the expansion area of the skin graft 14 through the camera 20 or from the amount of movement of the clamp connection rod 12 attached to the clamp module 11 and then measures the extent of the variation of the skin graft using the expanded area of the skin graft over time and the force applied to the skin graft.

A ratio of the expanded area based on the expansion area of the skin and the pressure versus the applied pressure may be determined by Equation 1 below.

$$S = \frac{\frac{(L-L_0)}{L_0}}{\frac{(P-P_0)}{P_0}}$$ [Equation 1]

$$S = \frac{(L-L_0)}{(P-P_0)}$$

Here, S is the expansion function of skin graft, $L_0$ is the skin area before the expansion, L is the expanded skin area, $P_0$ is the initial pressure applied, and P is the increased pressure.

A saturated expansion area of the skin graft is checked through the gradient of the S, and a maximum force is applied to a point just before the skin graft 14 is ruptured according to the saturated expansion area.

A method of expanding skin according to the embodiment of the present invention corresponding to the apparatus for expanding skin according to the above-described embodiment of the present invention will be described step by step with reference to FIG. 8.

Figure 8:
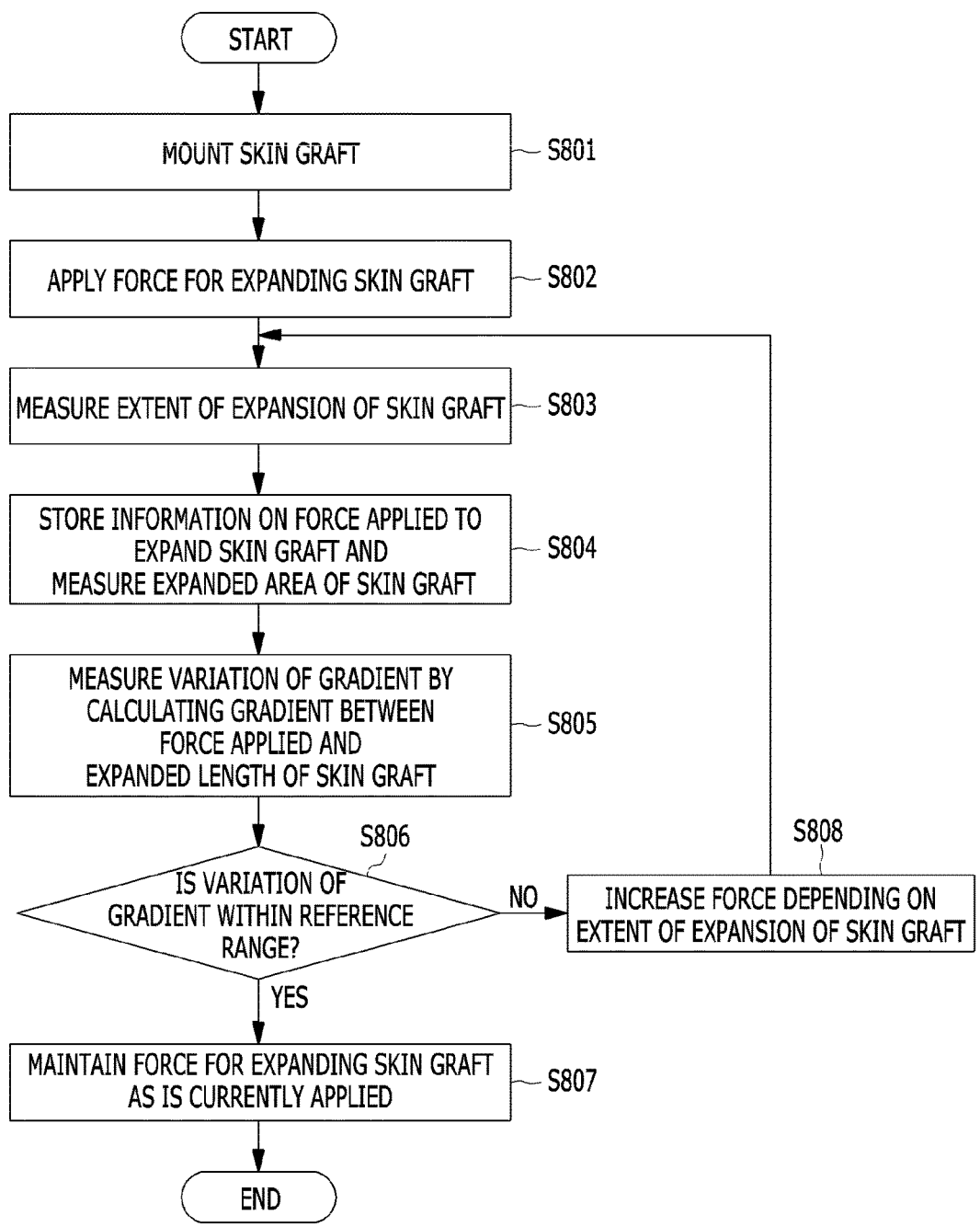
FIG. 8 is an operation flowchart illustrating a method of expanding skin according to the embodiment of the present invention.

FIG. 8 is an operation flowchart illustrating a method for expanding skin using the apparatus for expanding skin according to the embodiment of the present invention.

As illustrated in FIG. 8, first, the graft skin is mounted at the clamp in the skin graft expansion/culture chamber in which a culture medium is contained for the expansion and culturing (S801).

Next, a gradually increasing force to expand the skin graft mounted is applied starting from a predetermined initial force (S802).

Next, an extent to which the skin graft expands is measured by a camera or a sensor (S803).

Next, an expanded area of the skin graft is calculated for the extent of the expansion of the skin graft measured by the camera or the sensor (S804). Here, information on the force applied to expand the skin graft may be separately stored in a memory.

Next, a gradient for the force applied to expand the skin graft and the expanded length of the skin graft is calculated to measure a gradient variation (S805).

Next, whether the amount of variation amount of the gradient measured falls within a preset reference range is determined (S806). That is, through the variation of the gradient, the saturation point of the tensile force, for example, whether the gradient to be the point of "0" or "-", is determined.

As the result of the determination, when the variation of the gradient reaches "0" or "-", it is determined that the skin graft has expanded to the maximum extent, and the force level as currently applied to the skin graft is maintained (S807).

However, when the variation of the gradient has not reached "0" or "-", it is determined that the skin graft has not expanded to the maximum extent, and the force applied to the skin graft is increased depending on the extent of the expansion of the skin graft (S808).

As described above, when a variation of the gradient reaches "0" or "-", that is, the skin graft is determined to have expanded to the maximum extent, the culturing process of the skin graft 14 starts at the point.

An embodiment of the present invention may be implemented in a computer system, e.g., as a computer readable medium.

Figure 9:
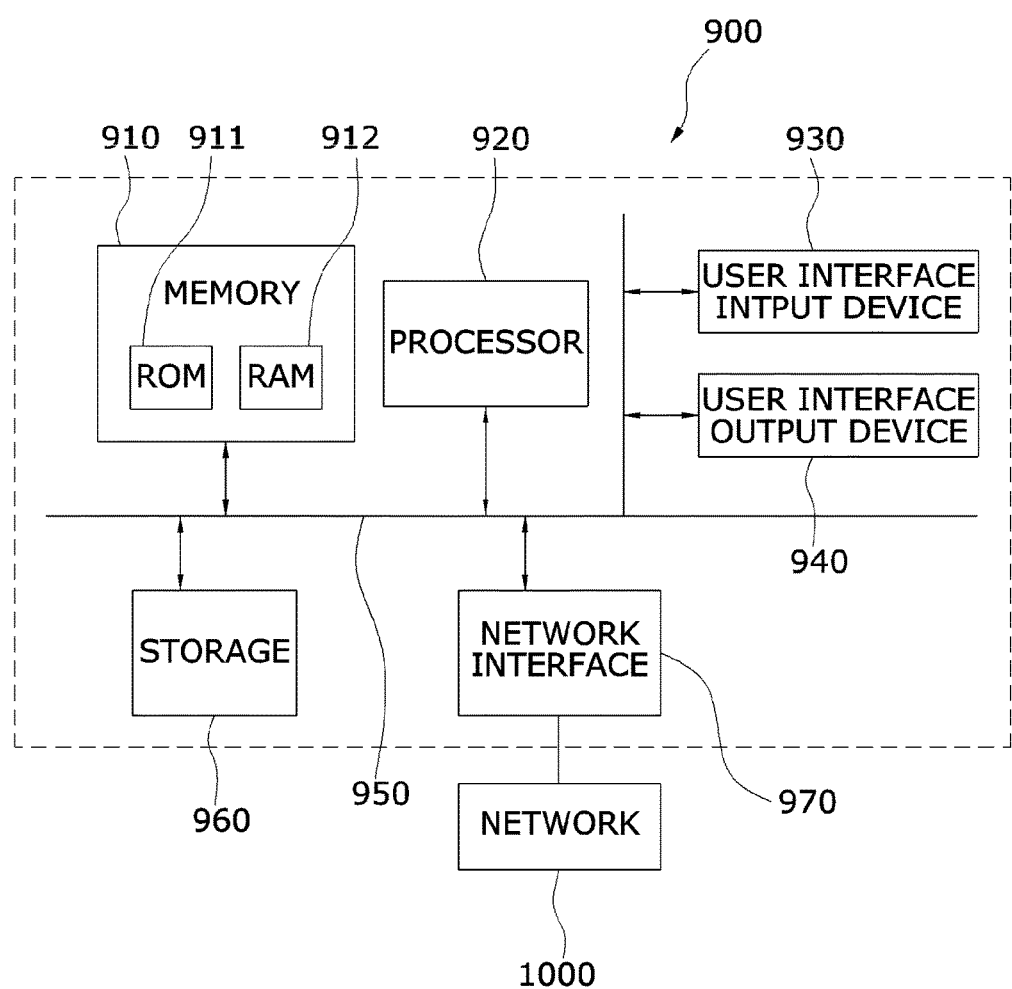
FIG. 9 is a block diagram illustrating a computer system to which the present invention is applied.

FIG. 9 is a block diagram illustrating a computer system to which the present invention is applied.

As shown in FIG. 9, a computer system 900 may include one or more of a processor 910, a memory 930, a user input device 940, a user output device 950, and a storage 960, each of which communicates through a bus 920. The computer system 900 may also include a network interface 970 that is coupled to a network 1000. The processor 910 may be a central processing unit (CPU) or a semiconductor device that executes processing instruction stored in the memory 930 and/or the storage 960. The memory 930 and the storage 960 may include various forms of volatile or non-volatile storage media. For example, the memory 930 may include a read-only memory (ROM) 931 and a random access memory (RAM) 932.

Accordingly, an embodiment of the invention may be implemented as a computer implemented method or as a non-transitory computer readable medium with computer executable instruction stored thereon. In an embodiment, when executed by the processor, the computer readable instruction may perform a method according to at least one aspect of the invention.

The apparatus and method for expanding skin according to the embodiment of the present invention is for expanding an area of a skin graft to the maximum extent by providing a stretching stimulus to the skin graft using tensile force. In addition, for performing a skin-grafting surgery, the apparatus and method can, outside of the body, expand and culture a small area of an autologous skin graft collected from a donor site to the maximum area possible safely while preventing necrosis of the skin and without rupturing the skin.

In other words, while an apparatus for expanding autologous skin outside the body in general takes a form of expanding skin by applying a certain amount of constant force for a period of time regardless of the skin properties, the apparatus and method for expanding skin according to the embodiment of the present invention can expand skin to the maximum extent to just before rupturing based on checking the elasticity of the skin through measurements to find the maximum area possible for expansion without rupturing.

While the apparatus and the method for expanding skin according to the present invention has been described with reference to the above embodiments, it is to be understood that the present invention is not limited to the disclosed embodiments, and it should be obvious to those skilled in the art that various modifications and other equivalent embodiments may be made without departing from the principles and sprit of the present invention.

Accordingly, the above-described embodiments of the present invention and the accompanying drawings should be considered in a descriptive sense only and not for the purposes of providing limitations, and the scope of the concept of the present invention is not limited by the above-described embodiments and the accompanying drawings. The scope of the present invention shall be interpreted only according to the technical sprit of the attached claims, and it should be understood that all technical sprit within equivalent scope thereof shall be interpreted to be included in the scope of the present invention.

What is claimed is:

1. An apparatus for expanding skin, comprising:
    a plurality of clamps adapted to clamp the skin, each of the plurality of clamps comprising:
        an upper plate which comes in contact with an upper surface of the skin graft;
        a lower plate which comes in contact with a lower surface of the skin graft; and
        at least one needle which protrudes from at least one of the upper plate and the lower plate and penetrates through the skin graft,
    a skin graft expansion/culture chamber in which a skin graft is clamped by the plurality of clamps to expand and be cultured;
    a driving control unit which drives the plurality of clamps of the skin graft expansion/culture chamber to expand the mounted skin graft and controls the driving of the plurality of clamps in the skin graft expansion/culture chamber depending on the extent of the expansion of the skin graft, the driving control unit comprising:
        a driving portion which applies a force to the plurality of clamps;
        a measurement portion which determines a gradient between the force applied to the plurality of clamps and a displacement of the skin graft retained by the plurality of clamps by increasing an amount of force applied to the skin graft and measuring the displacement of the skin graft resulting from the force; and
        a control portion which applies a constant force to the skin graft when the gradient reaches zero.

2. The apparatus of claim 1, wherein the plurality of clamps of the skin graft expansion/culture chamber drive in directions different from each other to expand the skin graft according to the control of the driving control unit.

3. The apparatus of claim 1, wherein the skin graft expansion/culture chamber includes:
    a detachable clamp module; and
    a clamp connection rod connected to the clamp module and each of the clamps and configured to slidingly drive to expand the skin graft in different directions.

4. The apparatus of claim 3, wherein the driving control unit modifies a position of at least one of the clamp module and the clamp connection rod to control expansion direction and expansion time of the skin graft.

5. The apparatus of claim 1, further comprising a monitoring unit which monitors the displacement the skin graft clamped by the plurality of clamps.

* * * * *